United States Patent
Thompson et al.

(10) Patent No.: US 7,482,451 B2
(45) Date of Patent: Jan. 27, 2009

(54) ORGANIC LIGHT EMITTING MATERIALS WITH ANIONIC LIGAND

(75) Inventors: Mark E. Thompson, Anaheim Hills, CA (US); Peter Djurovich, Long Beach, CA (US); Jian Li, Los Angeles, CA (US)

(73) Assignee: The University of Southern California, Los Angeles, CA (US)

( * ) Notice: Subject to any disclaimer, the term of this patent is extended or adjusted under 35 U.S.C. 154(b) by 875 days.

(21) Appl. No.: 10/643,697

(22) Filed: Aug. 18, 2003

(65) Prior Publication Data
US 2004/0102632 A1    May 27, 2004

Related U.S. Application Data

(60) Provisional application No. 60/404,087, filed on Aug. 16, 2002.

(51) Int. Cl.
*C07F 15/00* (2006.01)
*C07F 5/02* (2006.01)
*C07D 207/00* (2006.01)
*B01J 31/00* (2006.01)

(52) U.S. Cl. ............... 546/4; 546/11; 546/13; 548/403; 502/162; 502/167; 502/200

(58) Field of Classification Search ........ 546/4, 546/11, 13; 502/167, 166, 206; 548/403
See application file for complete search history.

(56) References Cited

U.S. PATENT DOCUMENTS

| | | |
|---|---|---|
| 4,769,292 A | 9/1988 | Tang et al. |
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,087,982 A | 7/2000 | Liu |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 2002/0182441 A1* | 12/2002 | Lamansky et al. .......... 428/690 |
| 2003/0230980 A1 | 12/2003 | Forrest et al. |

OTHER PUBLICATIONS

Fernandez et al, Polyhedron, v. 10 No. 14 pp. 1595-1598 (1991), Poly(1-pyrazolyl)boratoriridium and tris(1-pyrazolylmethyl) aminoiridium and -rhodium complexes.*

(Continued)

*Primary Examiner*—Janet L. Andres
*Assistant Examiner*—Raymond Covington
(74) *Attorney, Agent, or Firm*—Kenyon & Kenyon LLP (57) ABSTRACT

Emissive phosphorescent organometallic compounds that produce electroluminescence and organic light emitting devices employing such emissive phosphorescent organometallic compounds are provided. More specifically the present invention is directed to novel primarily non-emitting ligands which produce a blue shift in emitted light when associated with a cyclometallated ligand.

12 Claims, 2 Drawing Sheets

OTHER PUBLICATIONS

Onishi et al, Chem. Let. pp. 956-958 Platinum (II) polypyrazolyborate complexes containing a Pd-C bond. (1976).*

Concise Encclopedia Chemistry, (1993), pp. 490.*

Baldo et al., "Highly Efficient Phosphorescent Emission from Organic Electroluminescent Devices", Nature, vol. 395, pp. 151-154, 1998.

Baldo et al., "Very High Efficiency Green Organic Light Emitting Devices based on Electrophosphorescence", Appl. Phys. Letter vol. 75, No. 3, pp. 4-6 (1999).

Adachi et al., "Nearly 100% Internal Phophorescent Efficiency in an Organic Light Emitting Device", J. Appl. Phys., 90, 5048 (2001).

H. J. A. Dartnall et al., Proc. Roy. Soc. B. (London), 1983, 220, pp. 115-130.

Lu et al., U.S. Appl. No. 09/931,948, filed Aug. 20, 2001, entitled "Transparent Electrodes".

Shtein, et al., U.S. Appl. No. 10/233,470, filed Sep. 4, 2002, entitled "Process and apparatus for Organic Vapor Jet Deposition".

* cited by examiner

ORGANIC LIGHT EMITTING MATERIALS WITH ANIONIC LIGAND

This application is related to and claims priority from U.S. Provisional Patent Application 60/404,087, filed Aug. 16, 2002, which is incorporated herein in its entirety.

GOVERNMENT RIGHTS

This invention was made with Government support under Contract No. F33615-94-1-1414 awarded by DARPA. The government has certain rights in this invention.

RESEARCH AGREEMENTS

The claimed invention was made by, on behalf of, and/or in connection with one or more of the following parties to a joint university-corporation research agreement: Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention is directed to phosphorescence based organic light emitting materials and devices that have improved electroluminescent characteristics. More specifically, the present invention relates to materials and devices that are, for example, capable of emitting in the blue region of the visible spectrum.

BACKGROUND

Opto-electronic devices that make use of organic materials are becoming increasingly desirable for a number of reasons. Many of the materials used to make such devices are relatively inexpensive. Consequently, organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be an fluorescent or phosphorescent small molecule emitter. A dendrimer may be a "small molecule," and it is believed that all dendrimers currently used in the field of OLEDs are small molecules.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

OLED devices are generally (but not always) intended to emit light through at least one of the electrodes, and one or more transparent electrodes may be useful in an organic opto-electronic device. For example, a transparent electrode material, such as indium tin oxide (ITO), may be used as the bottom electrode. A transparent top electrode, such as disclosed in U.S. Pat. Nos. 5,703,436 and 5,707,745, which are incorporated by reference in their entireties, may also be used. For a device intended to emit light only through the bottom electrode, the top electrode does not need to be transparent, and may be comprised of a thick and reflective metal layer having a high electrical conductivity. Similarly, for a device intended to emit light only through the top electrode, the bottom electrode may be opaque and/or reflective. Where an electrode does not need to be transparent, using a thicker layer may provide better conductivity, and using a reflective electrode may increase the amount of light emitted through the other electrode, by reflecting light back towards the transparent electrode. Fully transparent devices may also be fabricated, where both electrodes are transparent. Side emitting OLEDs may also be fabricated, and one or both electrodes may be opaque or reflective in such devices.

As used herein, "top" means furthest away from the substrate, while "bottom" means closest to the substrate. For example, in a device having two electrodes, the bottom electrode is the electrode closest to the substrate, and is generally the first electrode fabricated. The bottom electrode has two surfaces, a bottom surface closest to the substrate, and a top surface further away from the substrate. Where a first layer is described as "disposed over" a second layer, the first layer is disposed further away from substrate. There may be other layers between the first and second layer, unless it is specified that the first layer is "in physical contact with" the second layer. For example, a cathode may be described as "disposed over" an anode, even though there are various organic layers in between.

The technology of organic light emitting diodes (OLEDs) is undergoing rapid development. OLEDs originally utilized the electroluminescence produced from electrically excited molecules that emitted light from their singlet states as disclosed, for example, in U.S. Pat. No. 4,769,292. Such radiative emission from a singlet excited state is referred to as fluorescence. More recent work has demonstrated that higher power efficiency OLEDs can be made using molecules that emit light from their triplet state, defined as phosphorescence. Such electrophosphorescence makes it possible for phosphorescent OLEDs to have substantially higher quantum efficiencies than are possible for OLEDs that only produce fluorescence. This is based on the understanding that the excitons created in an OLED are produced, according to simple statistical arguments as well as experimental measurements, approximately 75% as triplet excitons and 25% as singlet excitons. The triplet excitons more readily transfer their energy to triplet excited states that can produce phosphorescence whereas the singlet excitons typically transfer their energy to singlet excited states that can produce fluorescence.

Since the lowest emissive singlet excited state of an organic molecule is typically at a slightly higher energy than the lowest triplet excited state, the singlet excited state may relax, by an intersystem crossing process, to the emissive triplet excited state. This means that all the exciton excitation energy may be converted into triplet state excitation energy, which then becomes available as phosphorescent emission. Thus, electrophosphorescent OLEDs have a theoretical quantum efficiency of 100%, since all the excitation energy can become available as electrophosphorescence.

In contrast, only a small percentage (about 25%) of excitons in fluorescent devices are capable of producing the fluorescent luminescence that is obtained from a singlet excited state. The remaining excitons in a fluorescent device, which are produced in the lowest triplet excited state of an organic molecule, are typically not capable of being converted into the energetically unfavorable higher singlet excited states from which the fluorescence is produced. This energy, thus, becomes lost to radiationless decay processes that heat-up the device.

As a consequence, since the discovery that phosphorescent materials could be used-in an OLED, Baldo et al., "*Highly Efficient Phosphorescent Emission from Organic Electroluminescent Devices*", Nature, vol. 395, 151-154, 1998, there is now much interest in finding more efficient electrophosphorescent materials. OLEDs utilizing phosphorescent materials are disclosed, for example, in U.S. Pat. No. 6,303,238 which is incorporated by reference in its entirety.

Typically, phosphorescent emission from organic molecules is less common than fluorescent emission. However, phosphorescence can be observed from organic molecules under an appropriate set of conditions. It would be desirable if more efficient electrophosphorescent materials could be found, particularly materials that produce their emission in the technologically useful blue and green colors of the visible spectrum.

SUMMARY OF THE INVENTION

The present invention is directed to emissive phosphorescent organometallic compounds that produce improved electroluminescence, organic light emitting devices employing such emissive phosphorescent organometallic compounds. More specifically the present invention is directed to novel primarily non-emitting ligands which produce a blue shift in emitted light when associated with a cyclometallated ligand.

Specific embodiments of the present invention are directed to OLEDs using emissive phosphorescent organometallic compounds that produce improved electrophosphorescence in the blue region of the visible spectrum.

DESCRIPTION OF THE INVENTION

The present invention will now be described in detail for specific preferred embodiments of the invention. These embodiments are intended to be illustrative and the invention is not limited in scope to the specific preferred embodiments described.

The present invention relates to OLEDs that efficiently emit light, in particular, that preferably emit light in the blue range of the visible spectrum, and to the phosphorescent emissive materials used in the devices. The invention also relates to non-emitting ligands that produce a hypsochromic (blue) shift in the emission spectrum of light emitted by an associated emitting ligand.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151 154, 1998; ("Baldo I") and Baldo et al., "Very high efficiency green organic light emitting devices based on electrophosphorescence," Appl. Phys. Lett., vol. 75, No. 3, 4 6 (1999) ("Baldo II"), which are incorporated by reference in their entireties. Phosphorescence may be referred to as a "forbidden" transition because the transition requires a change in spin states, and quantum mechanics indicates that such a transition is not favored. As a result, phosphorescence generally occurs in a time frame exceeding at least 10 nanoseconds, and typically greater than 100 nanoseconds. If the natural radiative lifetime of phosphorescence is too long, triplets may decay by a non-radiative mechanism, such that no light is emitted. Organic phosphorescence is also often observed in molecules containing heteroatoms with unshared pairs of electrons at very low temperatures. 2,2' bipyridine is such a molecule. Non-radiative decay mechanisms are typically temperature dependent, such that a material that exhibits phosphorescence at liquid nitrogen temperatures may not exhibit phosphorescence at room temperature. But, as demonstrated by Baldo, this problem may be addressed by selecting phosphorescent compounds that do phosphoresce at room temperature.

Generally, the excitons in an OLED are believed to be created in a ratio of about 3:1, i.e., approximately 75% triplets and 25% singlets. See, Adachi et al., "Nearly 100% Internal Phosphorescent Efficiency In An Organic Light Emitting Device," J. Appl. Phys., 90, 5048 (2001), which is incorporated by reference in its entirety. In many cases, singlet excitons may readily transfer their energy to triplet excited states via "intersystem crossing," whereas triplet excitons may not readily transfer their energy to singlet excited states. As a result, 100% internal quantum efficiency is theoretically possible with phosphorescent OLEDs. In a fluorescent device, the energy of triplet excitons is generally lost to radiationless decay processes that heat up the device, resulting in much lower internal quantum efficiencies. OLEDs utilizing phosphorescent materials that emit from triplet excited states are disclosed, for example, in U.S. Pat. No. 6,303,238, which is incorporated by reference in its entirety.

Phosphorescence may be preceded by a transition from a triplet excited state to an intermediate non-triplet state from which the emissive decay occurs. For example, organic molecules coordinated to lanthanide elements often phosphoresce from excited states localized on the lanthanide metal. However, such materials do not phosphoresce directly from a triplet excited state but instead emit from an atomic excited state centered on the lanthanide metal ion. The europium diketonate complexes illustrate one group of these types of species.

Phosphorescence from triplets can be enhanced over fluorescence by confining, preferably through bonding, the organic molecule in close proximity to an atom of high atomic number. This phenomenon, called the heavy atom effect, is created by a mechanism known as spin orbit coupling. Such a phosphorescent transition may be observed from an excited metal to ligand charge transfer (MLCT) state of an organometallic molecule such as tris(2 phenylpyridine)iridium(III). Molecules that phosphoresce from MLCT triplet states, However, typically emit light that is of lower energy than that observed from the unbound organic ligand. This lowering of emission energy presents a challenge in the development of organic molecules that phosphoresce in the technologically useful blue and green colors of the visible spectrum where the unperturbed phosphorescence typically occurs.

Figure 1:
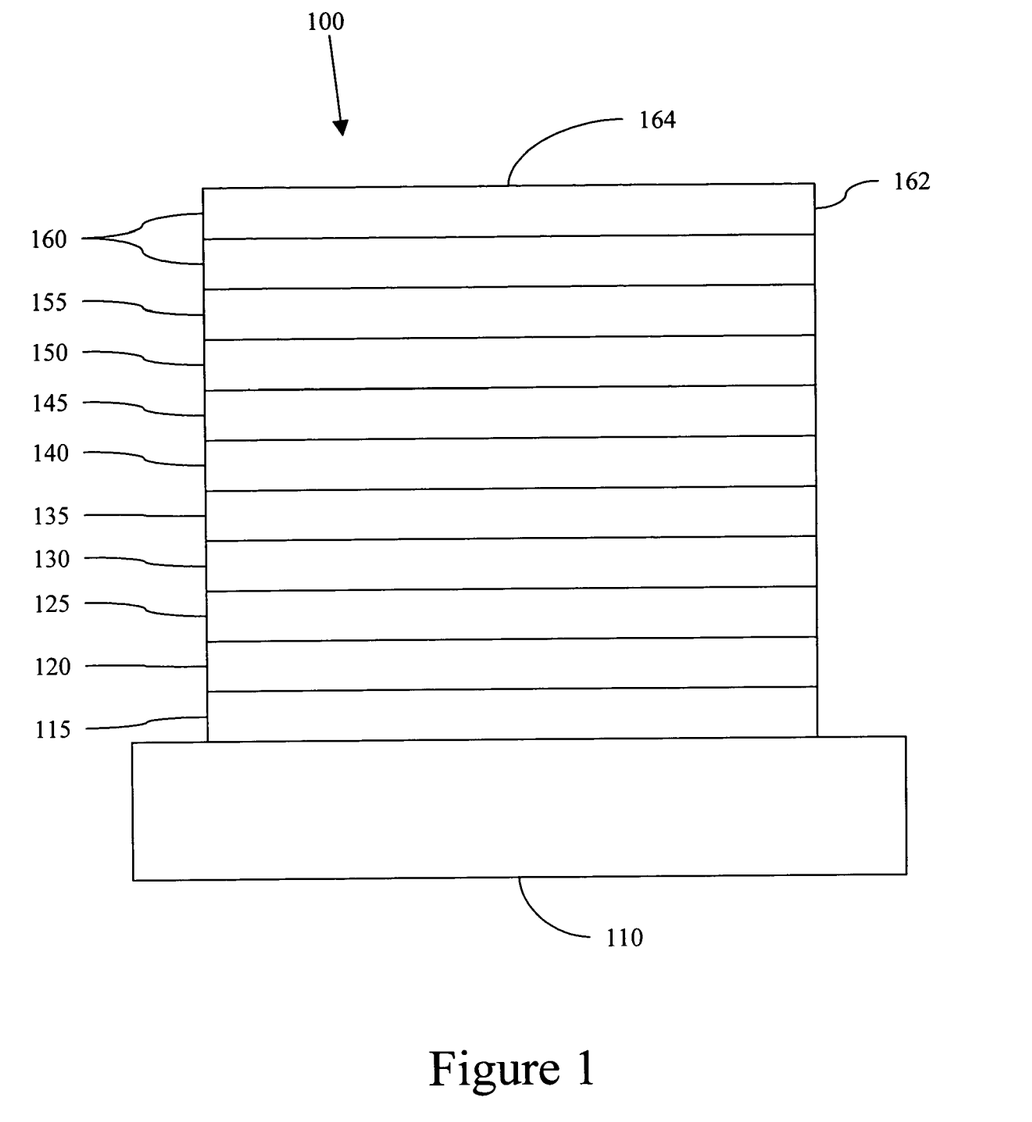
FIG. 1 shows an organic light emitting device having separate electron transport, hole transport, and emissive layers, as well as other layers.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order.

Substrate 110 may be any suitable substrate that provides desired structural properties. Substrate 110 may be flexible or rigid. Substrate 110 may be transparent, translucent or opaque. Plastic and glass are examples of preferred rigid substrate materials. Plastic and metal foils are examples of preferred flexible substrate materials. Substrate 110 may be a semiconductor material in order to facilitate the fabrication of circuitry. For example, substrate 110 may be a silicon wafer upon which circuits are fabricated, capable of controlling OLEDs subsequently deposited on the substrate. Other substrates may be used. The material and thickness of substrate 110 may be chosen to obtain desired structural and optical properties.

Anode 115 may be any suitable anode that is sufficiently conductive to transport holes to the organic layers. The material of anode 115 preferably has a work function higher than about 4 eV (a "high work function material"). Preferred anode materials include conductive metal oxides, such as indium tin oxide (ITO) and indium zinc oxide (IZO), aluminum zinc oxide (AlZnO), and metals. Anode 115 (and substrate 110) may be sufficiently transparent to create a bottom-emitting device. A preferred transparent substrate and anode combination is commercially available ITO (anode) deposited on glass or plastic (substrate). A flexible and transparent substrate-anode combination is disclosed in U.S. Pat. No. 5,844,363, which is incorporated by reference in its entirety. Anode 115 may be opaque and/or reflective. A reflective anode 115 may be preferred for some top-emitting devices, to increase the amount of light emitted from the top of the device. The material and thickness of anode 115 may be chosen to obtain desired conductive and optical properties. Where anode 115 is transparent, there may be a range of thickness for a particular material that is thick enough to provide the desired conductivity, yet thin enough to provide the desired degree of transparency. Other anode materials and structures may be used.

Hole transport layer 125 may include a material capable of transporting holes. Hole transport occurs predominantly through the highest occupied molecular orbital (HOMO) levels of the "charge carrying component" of the hole transporting layer. This component may be the base material of the hole transport layer 125, or it may be a dopant. Hole transport layer 125 may be intrinsic (undoped), or doped. Doping may be used to enhance conductivity. α-NPD and TPD are examples of intrinsic hole transport layers. An example of a p-doped hole transport layer is m-MTDATA doped with F4-TCNQ at a molar ratio of 50:1, as disclosed in U.S. patent application Ser. No. 10/173,682 to Forrest et al., which is incorporated by reference in its entirety. Other hole transport layer materials and structures may be used.

As disclosed herein, emissive layer 135 includes an organic material capable of emitting photons of light when electrons drop from a lowest unoccupied molecular orbital (LUMO) of layer 135 where they combine with holes in the highest occupied molecular orbital of layer 135. Accordingly, a current flow passed between anode 115 and cathode 160 through emissive layer 135 can produce an emission of light. In a present embodiment, emissive layer 135 comprises a phosphorescent emissive material such as those disclosed herein. Phosphorescent materials are preferred over fluorescenct materials because of the higher luminescent efficiencies associated with such materials.

Emissive layer 135 may comprise a host material capable of transporting electrons and/or holes, doped with an emissive material that may trap electrons, holes, and/or excitons, such that excitons relax from the emissive material via a photoemissive mechanism. Emissive layer 135 may comprise a single material that combines transport and emissive properties. Whether the emissive material is a dopant or a major constituent, emissive layer 135 may comprise other materials, such as dopants that tune the emission of the emissive material. Emissive layer 135 may include a plurality of emissive materials capable of, in combination, emitting a desired spectrum of light. Examples of phosphorescent emissive materials include Ir(ppy)$_3$. Examples of fluorescent emissive materials include DCM and DMQA. Examples of host materials include Alq$_3$, CBP and mCP. Examples of emissive and host materials are disclosed in U.S. Pat. No. 6,303,238 to Thompson et al., which is incorporated by reference in its entirety. Emissive material may be included in emissive layer 135 in a number of ways. For example, an emissive small molecule may be incorporated into a polymer. Other emissive layer materials and structures may be used.

Electron transport layer 140 may comprise a material capable of transporting electrons. Electron transport layer 140 may be intrinsic (undoped), or doped. Doping may be used to enhance conductivity. Alq$_3$ is an example of an intrinsic electron transport layer. An example of an n-doped electron transport layer material is BPhen doped with Li at a molar ratio of 1:1, as disclosed in U.S. patent application Ser. No. 10/173,682 to Forrest et al., which is incorporated by reference in its entirety. Other electron transport layers materials and structures may be used. The charge carrying component of the electron transport layer may be selected such that electrons can be efficiently injected from the cathode into the LUMO (Lowest Unoccupied Molecular Orbital) energy level of the electron transport layer. Electron transport occurs predominantly through the lowest unoccupied molecular orbit (LUMO) levels of the "charge carrying component" of the electron transport layer. The "charge carrying component" is the material responsible for the LUMO that actually transports electrons. This component may be the base material, or it may be a dopant. The LUMO level of an organic material may be generally characterized by the electron affinity of that material while the relative electron injection efficiency of a cathode may be generally characterized in terms of the work function of the cathode material. Accordingly, the preferred properties of an electron transport layer and the adjacent cathode may be specified in terms of the electron affinity of the charge carrying component of the ETL and the work function of the cathode material. In particular, so as to achieve high electron injection efficiency, the work function of the cathode material is preferably not greater than the electron affinity of the charge carrying component of the electron transport layer by more than about 0.75 eV, more preferably, by not more than about 0.5 eV. Similar considerations apply to any layer into which electrons are being injected.

Cathode 160 may be any suitable material or combination of materials known to the art, such that cathode 160 is capable of conducting electrons and injecting them into the organic layers of device 100. Cathode 160 may be transparent or opaque, and may be reflective. Metals and metal oxides are examples of suitable cathode materials. Cathode 160 may be a single layer, or may have a compound structure. FIG. 1 shows a compound cathode 160 having a thin metal layer 162 and a thicker conductive metal oxide layer 164. In a compound cathode, preferred materials for the thicker layer 164 include ITO, IZO, and other materials known to the art. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The part of cathode 160 that is in contact with the underlying organic layer, whether it is a single layer cathode 160, the thin metal layer 162 of a compound cathode, or some other part, is preferably made of a material having a work function lower than about 4 eV (a "low work function material"). Other cathode materials and structures may be used.

Blocking layers may be used to reduce the number of charge carriers (electrons or holes) and/or excitons that leave the emissive layer. An electron blocking layer 130 may be disposed between emissive layer 135 and the hole transport layer 125, to block electrons from leaving emissive layer 135 in the direction of hole transport layer 125. Similarly, a hole blocking layer 140 may be disposed between emissive layer 135 and electron transport layer 145, to block holes from leaving emissive layer 135 in the direction of electron transport layer 140. Blocking layers may also be used to block excitons from diffusing out of the emissive layer.

The theory and use of blocking layers is described in more detail in U.S. Pat. No. 6,097,147 and U.S. patent application Ser. No. 10/173,682 to Forrest et al., which are incorporated by reference in their entireties. The conventional "blocking layer" is generally believed to reduce the number of charge carriers and/or excitons that leave the emissive layer by presenting an energy barrier that the charge carrier or exciton has difficulty surmounting. For example, hole transport is generally thought to be related to the Highest Occupied Molecular Orbital (HOMO) of an organic semiconductor. A "hole blocking" material may therefore be generally considered as a material that has a HOMO energy level significantly less than that of the material from which the holes are being blocked. A first HOMO energy level is considered "less than" a second HOMO energy level if it is lower on a conventional energy level diagram, which means that the first HOMO energy level would have a value that is more negative than the second HOMO energy level. For example, according to the density functional theory (DFT) calculation (B3LYP 6-31G*) using the Spartan 02 software package, $Ir(ppy)_3$ has a HOMO energy level of −4.85 eV. BCP has a HOMO energy level of −5.87 eV, which is 1.02 eV less than that of $Ir(ppy)_3$, making it an excellent hole blocker. $ZrQ_4$ has a HOMO energy level of −5.00, only 0.15 eV less than that of $Ir(ppy)_3$, such that little or no hole blocking is expected. mer-$GaQ_3$ has a HOMO energy level of −4.63 eV, which is greater than that of $Ir(ppy)_3$, such that no hole blocking at all is expected.

If the emissive layer includes different materials with different energy levels, the effectiveness of these various materials as hole blocking layers may be different, because it is the difference in HOMO energy levels between the blocking layer and the blocked layer that is significant, not the absolute HOMO energy level. The absolute HOMO level, however, may be useful in determining whether a compound will be a good hole blocker for particular emissive layers. For example, a material having a HOMO energy level of about −5.15 eV or less may be considered a reasonable hole blocking material for Ir(ppy)3, which is a representative emissive material. Generally, a layer having a HOMO energy level that is at least 0.25 eV less than that of an adjacent layer may be considered as having some hole blocking properties. An energy level difference of at least 0.3 eV is preferred, and an energy level difference of at least 0.7 eV is more preferred. Similarly, the energy of an exciton is generally believed to be related to the band gap of a material. An "exciton blocking" material may generally be thought of as a material having a band gap significantly larger than the material from which excitons are being blocked. For example, a material having a band gap that is about 0.1 eV or more larger than that of an adjacent material may be considered a good exciton blocking material.

Generally, injection layers are comprised of a material that may improve the injection of charge carriers from one layer, such as an electrode or an organic layer, into an adjacent organic layer. Injection layers may also perform a charge transport function. In device 100, hole injection layer 120 may be any layer that improves the injection of holes from anode 115 into hole transport layer 125. CuPc is an example of a material that may be used as a hole injection layer from an ITO anode 115, and other anodes. In device 100, electron injection layer 150 may be any layer that improves the injection of electrons into electron transport layer 145. LiF/Al is an example of a material that may be used as an electron injection layer into an electron transport layer from an adjacent layer. Other materials or combinations of materials may be used for injection layers. Depending upon the configuration of a particular device, injection layers may be disposed at locations different than those shown in device 100. More examples of injection layers are provided in U.S. patent application Ser. No. 09/931,948 to Lu et al., which is incorporated by reference in its entirety. A hole injection layer may comprise a solution deposited material, such as a spin-coated polymer, e.g., PEDOT:PSS, or it may be a vapor deposited small molecule material, e.g., CuPc or MTDATA.

A hole injection layer (HIL) may planarize or wet the anode surface so as to provide efficient hole injection from the anode into the hole injecting material. A hole injection layer may also have a charge carrying component having HOMO (Highest Occupied Molecular Orbital) energy levels that favorably match up, as defined by their herein-described relative ionization potential (IP) energies, with the adjacent anode layer on one side of the HIL and the hole transporting layer on the opposite side of the HIL. Using a doped HIL allows the dopant to be selected for its electrical properties, and the host to be selected for morphological properties such as wetting, flexibility, toughness, etc. Preferred properties for the HIL material are such that holes can be efficiently injected from the anode into the HIL material. In particular, the charge carrying component of the HIL preferably has an IP not more than about 0.7 eV greater that the IP of the anode material. More preferably, the charge carrying component has an IP not more than about 0.5 eV greater than the anode material. Similar considerations apply to any layer into which holes are being injected. HIL materials are distinguished from conventional hole transporting materials that are typically used in the hole transporting layer of an OLED in that such HIL materials may have a hole conductivity that is substantially less than the hole conductivity of conventional hole transporting materials. The thickness of the HIL of the present invention may be thick enough to help planarize or wet the surface of the anode layer. For example, an HIL thickness of as little as 10 nm may be acceptable for a very smooth anode surface. However, since anode surfaces tend to be very rough, a thickness for the HIL of up to 50 nm may be desired in some cases.

A protective layer may be used to protect underlying layers during subsequent fabrication processes. For example, the processes used to fabricate metal or metal oxide top electrodes may damage organic layers, and a protective layer may be used to reduce or eliminate such damage. In device 100, protective layer 155 may reduce damage to underlying organic layers during the fabrication of cathode 160. Preferably, a protective layer has a high carrier mobility for the type of carrier that it transports (electrons in device 100), such that it does not significantly increase the operating voltage of device 100. CuPc, BCP, and various metal phthalocyanines are examples of materials that may be used in protective layers. Other materials or combinations of materials may be used. The thickness of protective layer 155 is preferably thick enough that there is little or no damage to underlying layers due to fabrication processes that occur after organic protective layer 160 is deposited, yet not so thick as to significantly increase the operating voltage of device 100. Protective layer 155 may be doped to increase its conductivity. For example, a CuPc or BCP protective layer 160 may be doped with Li. A more detailed description of protective layers may be found in U.S. patent application Ser. No. 09/931,948 to Lu et al., which is incorporated by reference in its entirety.

Figure 2:
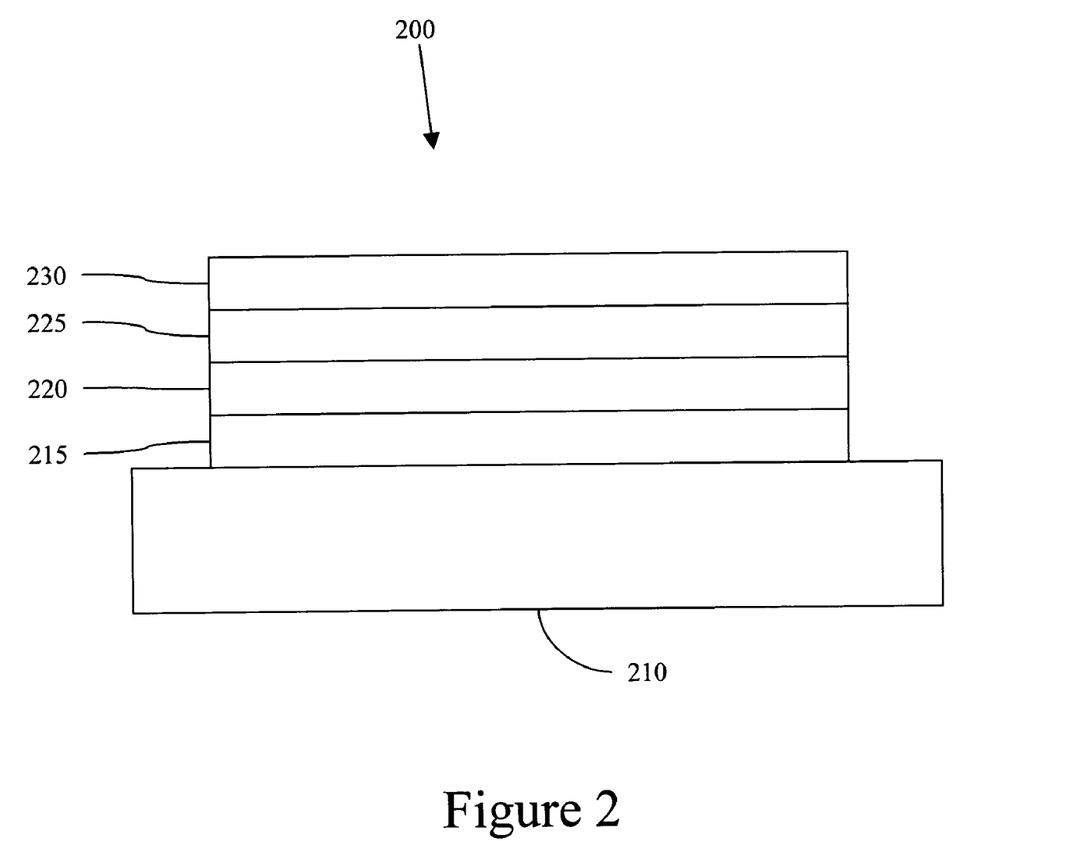
FIG. 2 shows an inverted organic light emitting device that does not have a separate electron transport layer.

FIG. 2 shows an inverted OLED 200. The device includes a substrate 210, an cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190, Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294, 398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

As used herein, "solution processible" means capable of being dissolved, dispersed, or transported in and/or deposited from a liquid medium, either in solution or suspension form.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art. CIE coordinates are described in H. Zollinger, "Color Chemistry" VCH Publishers, 1991 and H, J, A, Dartnall, J. K. Bowmaker, and J. D. Mollon, Proc. Roy. Soc. B (London), 1983, 220, 115-130, which are incorporated by reference. For example, the NTSC standard calls for a saturated blue having CIE (0.155, 0.07). The SRGB standard calls for CIE (0.15, 0.06). Other industry standards may call for slightly different CIE coordinates.

The present invention will now be described in detail for specific preferred embodiments of the invention. These embodiments are intended to be illustrative and the invention is not limited in scope to the specific preferred embodiments described.

The devices of the present invention comprise at least one phosphorescent organometallic emissive material. The emissive material comprises one or more ligands that produce a hypsochromic (blue) shift in the emission spectrum of light emitted by an associated emitting ligand. Organometallic compound of the present invention can be represented by the following general structure Formula I:

in which C—N is a cyclometallated ligand, M is a metal with an atomic weight of greater than 40, X and Y are independently selected groups incorporating a heteroatom, Z is a divalent linker, and m and n are integers selected from 1 and 2. The sum of n+m is 2 or 3. X-Z-Y is an anionic ligand. Preferably, M has an atomic weight of greater than 72.

The compounds of the present invention comprises a transition metal which produces phosphorescent emission from a mixture of MLCT and π-π* ligand states. Suitable transition metals include but are not limited to Ir, Pt, Pd, Rh, Re, Os, Tl, Pb, Bi, In, Sn, Sb, Te, Au, and Ag and other heavy metals with an atomic number of at least 40.

The divalent linker, Z, can be represented by the general structure $JR'_pR''_q$ wherein J is hydrogen or a metal or non-metal, selected as appropriate to bond to X and Y, R' and R" are independently H, alkyl, aryl, heteroaryl, halogen, hydroxy, alkoxy, aryloxy, amino, alkylamino, arylamino, sulfido, alkylsulfido, arylsulfido, phophino, alkylphosphino or arylphosphino and p and q are integers between 0 and 2. Without limiting the scope of the invention, Z can therefore be H, Ag, Au, BR'R", AlR'R" or ZnR' where R' and R" can be selected from the group consisting of alkyl, aryl and heteroaryl, and R' and R" can be interlinked to form a bidentate ligand. Preferably R' and R" are $C_1$-$C_6$ alkyl, aryl, heteroaryl, hydroxy, alkoxy, aryloxy, amino, alkylamino, arylamino, sulfido, alkylsulfido, arylsulfido, phosphino, alkylphosphino or arylphosphino. More preferably R' and R" are $C_1$-$C_3$ alkyl, aryl, heteroaryl, alkoxy, aryloxy, alkylamino, arylamino, alkylsulfido, arylsulfido, alkylphosphino or arylphosphino.

In one embodiment, the formal negative charge is located on the J in $JR'_pR''_q$. Such a chemical structure implies that the X—Ir and the Y—Ir bond are both dative bonds in nature. As a result, there is a formal positive charge on the Ir atom:

In such a Zwitterionic structure, it is believed that a blue shift of the metal complex phosphorescence can result. For example, as shown in Table 1, the emission peak of entry 3 is "blue shifted" by 30 nm relative to the comparative example which has a traditional acetylacetonate (acac) ancillary ligand.

In a preferred embodiment of the present invention, X and Y are heterocycles selected to have functionality appropriate for coordinating to M. In a further preferred embodiment X and Y are selected from the group consisting of pyrazoles, triazoles, tetrazoles, thiazoles, furans and pyridines. X and Y can be the same or different.

In a further embodiment of the present invention X and Y are selected from the group consisting of OR, SR, $NR_2$ and $PR_2$, wherein R is selected from the group consisting of H, alkyl, aryl, heteroaryl, halogen, alkoxy, amino, alkylamino, arylamino, sulfido, alkylsulfido, arylsulfido, phophino, alkylphosphino or arylphosphino In preferred embodiments of the present invention J is zinc, silver, gold, aluminum, boron or hydrogen. In more preferred embodiments J is boron or hydrogen.

The compounds of the present invention are, in a preferred embodiment, intended for use in a luminescent device. Generally such a device will comprise an organic layer which comprises the compound of the present invention disposed in some manner between two electrodes, one a cathode and the other an anode.

In a preferred embodiment the emissive layer comprises host material. The host material may comprise an electron transporting material that conducts charge primarily by the transport of electrons. Alternatively the host material may comprise a hole transporting material that conducts charge primarily by the transport of holes. The organometallic compound described can be doped in the host material of the light emitting device. The organometallic compound has a lowest triplet excited state with a radiative decay of greater than approximately $1 \times 10^5$ per second and the energy level of the lowest triplet excited state of the host material is higher than the energy level of the lowest triplet state of the organometallic compound. In a preferred embodiment of the present invention the energy difference between the lowest triplet excited state of the organometallic compound of the present invention and a corresponding relaxed state of the organometallic compound corresponds with a wavelength of less than approximately 520 nm. More preferably the energy difference between the lowest triplet excited state of the organometallic compound of the present invention and a corresponding relaxed state of the organometallic compound corresponds with a wavelength of between approximately 420 nm and approximately 480 nm.

The organic light emitting devices of the present invention may be fabricated using methods and materials known in the art. Representative OLED methods, materials and configurations are described in U.S. Pat. Nos. 5,703,436; 5,707,745; 5,834,893; 5,844,363; 6,097,147; and 6,303,238; each of which is incorporated by reference in its entirety.

The compounds described have been represented throughout by their monomeric structure. As is well known to those in the art, the compounds may also be present as dimers, trimers or dendrimers.

In one embodiment of the invention, the phosphorescent organometallic emissive material may be represented by the general formula II:

(II)

wherein also abbreviated C—N, is a cyclometallated ligand,

M is a metal with an atomic weight of greater than 40,

Z is a divalent linker, $R_2$ and $R_3$ are independently H, alkyl, aryl, heteroaryl, halogen, hydroxy, alkoxy, aryloxy, amino, alkylamino, arylamino, sulfido, alkylsulfido, arylsulfido, phophino, alkylphosphino or arylphosphino $R_a$, $R_b$, $R_c$, $R'_a$, $R'_b$ and $R'_c$, if present, are selected independently from H, alkyl, aryl, heteroaryl, halogen, alkoxy, amino, alkylamino, arylamino, sulfido, alkylsulfido, arylsulfido, phophino, alkylphosphino or arylphosphino, with the proviso that is anionic.

The ring structure represented by is a five- or six-membered ring comprising two adjacent nitrogens. The ring may also contain an additional hetero atom. Any two adjacent substituted positions on the ring may together form, independently, a fused 5- to 6-member cyclic group, wherein said cyclic group is cycloalkyl, cycloheteroalkyl, aryl, or heteroaryl. Z is a metal or non-metal, and preferably is Ag, Zn, Al, B, Ga, In, Cd, Hg, Cu, or Au.

In a further embodiment of the invention, X and Y are both a pyrazole or substituted pyrazole resulting in an emissive material having the Formula III:

III wherein C—N is a cyclometallated ligand, and M, Z, m and n are as described above for the Formula I. Each $R^{11}$ and $R^{12}$ is independently selected from alkyl, alkenyl, alkynyl, alkylaryl, CN, $CF_3$, $CO_2R$, C(O)R, $NR_2$, $NO_2$, OR, halo, aryl, heteroaryl, substituted aryl, substituted heteroaryl or a heterocyclic group, and additionally, or alternatively, any two adjacent substituted positions together form, independently, a fused 5- to 6-member cyclic group, wherein said cyclic group is cycloalkyl, cycloheteroalkyl, aryl, or heteroaryl, and wherein the fused 5- to 6-member cyclic group cyclic group may be optionally substituted with one or more of alkyl, alkenyl, alkynyl, alkylaryl, CN, $CF_3$, $CO_2R$, C(O)R, $NR_2$, $NO_2$, OR, or halo; each R is independently alkyl, alkenyl, alkynyl, aralkyl, and aryl; and subscript a and b are independently selected from 0, 1, 2, and 3.

In a further embodiment of the invention, X and Y are both a pyrazole and Z is H resulting in an emissive material of the formula IV:

wherein C—N is a cyclometallated ligand, and M, m and n are as described above for the Formula I. Each $R^{11}$ and $R^{12}$ is independently selected from alkyl, alkenyl, alkynyl, alkylaryl, CN, $CF_3$, $CO_2R$, $C(O)R$, $NR_2$, $NO_2$, OR, halo, aryl, heteroaryl, substituted aryl, substituted heteroaryl or a heterocyclic group, and additionally, or alternatively, any two adjacent substituted positions together form, independently, a fused 5- to 6-member cyclic group, wherein said cyclic group is cycloalkyl, cycloheteroalkyl, aryl, or heteroaryl, and wherein the fused 5- to 6-member cyclic group cyclic group may be optionally substituted with one or more of alkyl, alkenyl, alkynyl, alkylaryl, CN, $CF_3$, $CO_2R$, $C(O)R$, $NR_2$, $NO_2$, OR, or halo; each R is independently alkyl, alkenyl, alkynyl, aralkyl, and aryl; and subscript a and b are independently selected from 0, 1, 2, and 3.

In a preferred embodiment, the pyrazole rings of Formula IV are unsubstituted giving a compound of the formula $IV_a$:

wherein C—N is a cyclometallated ligand, and M, m and n are as described above for the Formula I. In a further preferred embodiment, M is Ir and m=2 and n=1.

A further embodiment of the invention is represented by the compound of Formula V:

wherein C—N is a cyclometallated ligand, and M, m and n are as described above for the Formula I. Each $R^{11}$, $R^{12}$, $R^{13}$, and $R^{14}$ is independently selected from alkyl, alkenyl, alkynyl, alkylaryl, CN, $CF_3$, $CO_2R$, $C(O)R$, $NR_2$, $NO_2$, OR, halo, aryl, heteroaryl, substituted aryl, substituted heteroaryl or a heterocyclic group, and additionally, or alternatively, any two adjacent substituted positions together form, independently, a fused 5- to 6-member cyclic group, wherein said cyclic group is cycloalkyl, cycloheteroalkyl, aryl, or heteroaryl, and wherein the fused 5- to 6-member cyclic group cyclic group may be optionally substituted with one or more of alkyl, alkenyl, alkynyl, alkylaryl, CN, $CF_3$, $CO_2R$, $C(O)R$, $NR_2$, $NO_2$, OR, or halo;

each R is independently alkyl, aryl and heteroarl; and subscript a, b, c, and d are independently selected from 0, 1, 2, and 3.

In a preferred embodiment, the pyrazole rings of Formula V are unsubstituted, M is Ir, m is 2 and n is 1, giving a compound of the formula $V_a$:

wherein C—N is a cyclometallated ligand.

In another embodiment of the invention the emissive material may be represented by the formula (VI)

wherein is a cyclometallated ligand,
M is a metal with an atomic weight of greater than 40,
Z is a divalent linker,
m is 1 or 2,
Q and Q' are heteroatoms, and,
$R_2$ and $R_3$ are hydrogen, halogens, heteroatoms or heterocycles.

The cyclometallated ligand, C—N, may be selected from those known in the art. Preferred cyclometallating ligands are 2-phenylpyridines and phenylpyrazoles and derivatives thereof. The phenylpyridine or phenylpyrazole cyclometallated ligand my be optionally substituted with one or more alkyl, alkenyl, alkynyl, alkylaryl, CN, $CF_3$, $CO_2R$, $C(O)R$, $NR_2$, $NO_2$, OR, halo, aryl, heteroaryl, substituted aryl, substituted heteroaryl or a heterocyclic group, and additionally, or alternatively, any two adjacent substituted positions together form, independently, a fused 5- to 6-member cyclic group, wherein said cyclic group is cycloalkyl, cycloheteroalkyl, aryl, or heteroaryl, and wherein the fused 5- to 6-member cyclic group cyclic group may be optionally substituted with one or more of alkyl, alkenyl, alkynyl, alkylaryl, CN, $CF_3$, $CO_2R$, $C(O)R$, $NR_2$, $NO_2$, OR, or halo; and each R is independently alkyl, alkenyl, alkynyl, aralkyl, and aryl;

In the present disclosure the following terms are used.

The term "halo" or "halogen" as used herein includes fluorine, chlorine, bromine and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted with one or more substituents selected from halo, CN, $CO_2R$, $C(O)R$, $NR_2$, cyclic-amino, $NO_2$, and OR.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted with one or more substituents selected from halo, CN, $CO_2R$, $C(O)R$, $NR_2$, cyclic-amino, $NO_2$, and OR.

The term "alkenyl" as used herein contemplates both straight and branched chain alkene radicals. Preferred alkenyl groups are those containing two to fifteen carbon atoms. Additionally, the alkenyl group may be optionally substituted with one or more substituents selected from halo, CN, $CO_2R$, $C(O)R$, $NR_2$, cyclic-amino, $NO_2$, and OR.

The term "alkynyl" as used herein contemplates both straight and branched chain alkyne radicals. Preferred alkyl groups are those containing two to fifteen carbon atoms. Additionally, the alkynyl group may be optionally substituted with one or more substituents selected from halo, CN, $CO_2R$, $C(O)R$, $NR_2$, cyclic-amino, $NO_2$, and OR.

The term "alkylaryl" as used herein contemplates an alkyl group which has as a substituent an aromatic group. Additionally, the alkylaryl group may be optionally substituted on the aryl with one or more substituents selected from halo, CN, $CO_2R$, $C(O)R$, $NR_2$, cyclic-amino, $NO_2$, and OR.

Cyclometallated ligand is a term well known in the art and includes but is not limited to MeOfppy, fppy, and $NMe_2$fppy.

Heterocyclic refers to a 3 to 7 membered ring containing at least one heteroatom. This includes aromatic rings including but not limited to pyrazole, triazole, tetrazole, thiazole, furan, thiophene, pyridine, and non-aromatic rings including but not limited to piperazine, piperidine, and pyrrolidine. The groups of the present invention can be substituted or unsubstituted. Preferred substituents include but are not limited to alkyl, alkoxy, aryl.

Heteroatom refers to S, O, N, P.

Preferred alkyl groups are $C_1$ through $C_6$ alkyls. Similarly $C_1$ through $C_6$ alkoxy and aryl groups are preferred. $C_1$ through $C_6$ heteroaryl, alkylamino, arylamino, alkylsulfido, arylsulfido, alkylphosphino or arylphosphino groups are preferable. More preferable are $C_1$ through $C_3$ alkyls. Similarly $C_1$ through $C_6$ alkoxy and aryl groups are preferred. $C_1$ through $C_6$ heteroaryl, alkylamino, arylamino, alkylsulfido, arylsulfido, alkylphosphino or arylphosphino.

Divalent linker refers to an atom or group to which two atoms or groups can be bonded such that overall the group X-Z-Y is one anionic ligand.

Pyrazole includes substituted or unsubstituted pyrazole.
Triazole includes substituted or unsubstituted triazole.
Tetrazole includes substituted or unsubstituted tetrazole.
Thiazole includes substituted or unsubstituted thiazole.
Pyridine includes substituted or unsubstituted pyridine.

Aryl alone or in combination includes carbocyclic aromatic systems or heterocyclic aromatic systems (also known as heteroaryl). The systems may contain one, two or three rings wherein each ring may be attached together in a pendent manner or may be fused. Preferably the rings have 5 or 6 members.

Alkoxy includes linear or branched alkoxy groups, preferably $C_1$ to $C_6$ alkoxy groups, more preferably $C_1$ to $C_3$ alkoxy groups.

Substituted refers to any level of substitution although mono-, di- and tri-substitutions are preferred. Preferred substituents include hydrogen, halogen, aryl, alkyl and heteroaryl.

pz is pyrazole.
MeOfppy is methoxy(difluorophenyl)pyridine.
fppy is (difluorophenyl)pyridine.
dmafppy is dimethylamino(difluorophenyl)pyridine.

Material Definitions

As used herein, abbreviations refer to materials as follows:

| | |
|---|---|
| CBP: | 4,4'-N,N-dicarbazole-biphenyl |
| m-MTDATA | 4,4',4''-tris(3-methylphenylphenlyamino)triphenylamine |
| Alq$_3$: | 8-tris-hydroxyquinoline aluminum |
| Bphen: | 4,7-diphenyl-1,10-phenanthroline |
| n-BPhen: | n-doped BPhen (doped with lithium) |
| F$_4$-TCNQ: | tetrafluoro-tetracyano-quinodimethane |
| p-MTDATA: | p-doped m-MTDATA (doped with F$_4$-TCNQ) |
| Ir(ppy)$_3$: | tris(2-phenylpyridine)-iridium |
| Ir(ppz)$_3$: | tris(1-phenylpyrazoloto,N,C(2')iridium(III) |
| BCP: | 2,9-dimethyl-4,7-diphenyl-1,10-phenanthroline |
| TAZ: | 3-phenyl-4-(1'-naphthyl)-5-phenyl-1,2,4-triazole |
| CuPc: | copper phthalocyanine. |
| ITO: | indium tin oxide |
| NPD: | N,N'-diphenyl-N-N'-di(1-naphthyl)-benzidine |
| TPD: | N,N'-diphenyl-N-N'-di(3-toly)-benzidine |
| BAlq: | aluminum(III)bis(2-methyl-8-quinolinato)4-phenylphenolate |
| mCP: | 1,3-N,N-dicarbazole-benzene |
| DCM: | 4-(dicyanoethylene)-6-(4-dimethylaminostyryl-2-methyl)-4H-pyran |
| DMQA: | N,N'-dimethylquinacridone |
| PEDOT: PSS: | an aqueous dispersion of poly(3,4-ethylenedioxythiophene) with polystyrenesulfonate (PSS) |
| ppz | 1-phenylpyrazole |
| ppy | 2-phenylpyridine |

It is understood that the various embodiments described herein are by way of example only, and are not intended to limit the scope of the invention. For example, many of the materials and structures described herein may be substituted with other materials and structures without deviating from the spirit of the invention. It is understood that various theories as to why the invention works are not intended to be limiting. For example, theories relating to charge transfer are not intended to be limiting.

The compounds described have been represented throughout by their monomeric structure. As is well known to those in the art, the compounds may also be present as dimers, trimers or dendrimers.

EXAMPLES

Synthesis of Compound 1: (MeOfppy)$_2$Ir(pz$_2$Bpz$_2$)

(MeOfppy)Ir(pz$_2$Bpz$_2$)

[Ir(MeOfppy)$_2$Cl]$_2$ (1.0 g, 0.75 mmol) was dissolved in 50 mL of CH$_2$Cl$_2$ and a solution of 2.1 equiv. AgOTf (0.41 g, 1.6 mmol) in 50 ml of MeOH was added to yield a cream-colored slurry. After the slurry was stirred for 2 hours at room temperature, it was centrifuged to precipitate the AgCl and the decantate was evaporated to dryness to yield a yellow, oily residue. The residue was dissolved in 50 ml CH$_3$CN, and 3 equiv. KBPz$_4$ (0.72 g, 2.26 mmol) was added to the solution. The solution was heated at 110 C for 18 hours under N$_2$, then filtered. The precipitate was washed with 50 mL CH$_2$Cl$_2$. The washed solution was collected and evaporated to dryness. Yield 0.8 g (MeOfPpy)$_2$Ir(pz$_2$Bpz$_2$). The filtrate of CH$_3$CN solution was evaporated to dryness. After chromatography, a second crop of (MeOfPpy)$_2$Ir(pz$_2$Bpz$_2$) about 0.2 g was obtained.

Synthesis of Compound 2: (MeOfppy)$_2$Ir(pz$_2$H)

(MeOfppy)Ir(pz$_2$H)

[Ir(MeOfppy)$_2$Cl]$_2$ (0.1 g, 0.075 mmol) was dissolved in 25 mL of CH$_2$Cl$_2$, 0.05 g pyrazole and 0.05 g excess MeONa were added to solution. After the solution was stirred for overnight at room temperature, it was filtered off. The filtrate was collected and evaporated to dryness. The crude product was recrystalized in CH$_2$Cl$_2$/MeOH to yield over 0.1 g clean (MeOfppy)$_2$Ir(pz$_2$H).

Synthesis of Compound 3: (fppy)$_2$Ir(pz$_2$Bpz$_2$)

(fppy)Ir(pz$_2$Bpz$_2$)

0.93 g [Ir(fppy)$_2$Cl]$_2$ was dissolved in 50 mL of CH$_2$Cl$_2$ and a solution of 0.5 g AgOTf in 50 ml of MeOH was added to yield a cream-colored slurry. After the slurry was stirred for 2 hours at room temperature, it was centrifuged to precipitate the AgCl and the decantate was evaporated to dryness to yield a yellow, oily residue. The residue was dissolved in 50 ml CH$_3$CN, and 0.85 KBPz$_4$ was added to the solution. The solution was heated at 110 C for 18 hours under N$_2$, then filtered. The precipitate was washed with 50 mL CH$_2$Cl$_2$. The washed solution was collected and evaporated to dryness. Yield 0.8 g (fppy)$_2$Ir(pz$_2$Bpz$_2$).

Synthesis of Compound 4: (dmafppy)$_2$Ir(pz$_2$BPz$_2$)

(dmafppy)Ir(pz$_2$Bpz$_2$)

0.1 g [Ir(dmafppy)$_2$Cl]$_2$ was dissolved in 15 mL of CH$_3$CN and 0.04 g AgOTf was added to yield a cream-colored slurry. After the slurry was stirred for 2 hours at room temperature, it was centrifuged to precipitate the AgCl. 0.07 g KBPz$_4$ was added to the decantante. The solution was heated at 110 C for 18 hours under N$_2$, then filtered. The precipitate was washed with 20 mL CH$_2$Cl$_2$. The washed solution was collected and evaporated to dryness. Yield 0.05 g (dmafppy)$_2$Ir(Pz$_2$Bpz$_2$).

Device Fabrication

Devices 1 and 3, and the comparative example were fabricated by high vacuum (<10$^{-7}$ Torr) thermal evaporation. Indium tin oxide (ITO) anode on glass was used as the anode. The cathode consists of 10 Å of LiF followed by 1,000 Å of Al. All devices were encapsulated with a glass lid sealed with an epoxy resin in a nitrogen glove box (<1 ppm of H$_2$O and O$_2$) immediately after fabrication, and a moisture getter was incorporated inside the package. The emission maxima and maximum luminous efficiency (in cd/A) are summarized in following Table. For compound 2 and 4, the emission maxima are obtained from the photoluminescence measured in CH$_2$Cl$_2$.

Device 1

The organic stack consists of, from the anode to the cathode, 100 Å of copper phthalocyanine (CuPc), 300 Å of 4,4'-bis[N-(1-naphthyl)-N-phenylamino]biphenyl (α-NPD), 300 Å of mCP doped with 6 wt % of Compound 1 as the emissive layer (EML), 400 Å of aluminum(III)bis(2-methyl-8-quinolinato)4-phenylphenolate (BAlq).

Device 3

The organic stack consists of, from the anode to the cathode, 100 Å of copper phthalocyanine (CuPc), 300 Å of 4,4'-bis[N-(1-naphthyl)-N-phenylamino]biphenyl (α-NPD), 300 Å of mCP doped with 6 wt % of Compound 3 as the emissive layer (EML), 400 Å of aluminum(III)bis(2-methyl-8-quinolinato)4-phenylphenolate (BAlq).

Comparative Example

The organic stack consists of, from the anode to the cathode, 100 Å of copper phthalocyanine (CuPc), 300 Å of 4,4'-bis[N-(1-naphthyl)-N-phenylamino]biphenyl (α-NPD), 300 Å of mCP doped with 6 wt % of the comparative example compound as the emissive layer (EML), 400 Å of aluminum(III)bis(2-methyl-8-quinolinato)4-phenylphenolate (BAlq).

TABLE 1

| | M | R2 | R3 | R4 | R5 | R'4 | R'5 | R'6 | (X) Ligand | Emission (nm) | OLED Max Efficiency (cd/A) |
|---|---|---|---|---|---|---|---|---|---|---|---|
| 1 | Ir | F | H | F | H | OMe | H | H | pz$_2$Bpz$_2$ | 450 | 3.5 |
| 2 | Ir | F | H | F | H | OMe | H | H | pz$_2$H | 462 | |
| 3 | Ir | F | H | F | H | H | H | H | pz$_2$Bpz$_2$ | 455 | 7 |
| 4 | Ir | F | H | F | H | NMe$_2$ | H | H | pz$_2$Bpz$_2$ | 448 | |
| Comparative Example | Ir | F | H | F | H | H | H | H | acac | 485 | 5 |

The invention claimed is:

1. A compound represented by the Formula (I)

(I)

wherein is a cyclometallated ligand,

M is a metal with an atomic weight of greater than 40,

X and Y are each an independently selected from pyrazoles, tetrazoles, thiazoles, furans and pyridines, Z is a group of the formula $JR'_p R''_q$ wherein J is hydrogen or a metal or a non-metal, R' and R" are independently, alkenyl, heteroaryl, hydroxy, alkoxy, aryloxy, amino, alkylamino, arylamino, sulfido, alkylsulfido, arylsulfido, phophino, alkylphosphino or arylphosphino and p and q are integers between 0 and 2.

m and n are integers selected from 1 and 2 wherein the sum of n+m is 3, with the proviso that is anionic.

2. The compound of claim 1, wherein J is boron.

3. The compound of claim 1 wherein R' and R" are selected from the group consisting of alkyls, aryls, and pyrazoles and p and q are each 1.

4. The compound of claim 3 wherein R' is pyrazole, R" is a pyrazole and p and q are each 1.

5. The compound of claim 1 wherein X and Y are pyrazoles.

6. The compound of claim 5, wherein Z is hydrogen.

7. The compound of claim 1, wherein the heavy metal is selected from the group consisting of Ir, Pt, Pd, Rh, Re, Os, Tl, Pb, Bi, In, Sn, Sb, Te, Ag, and Au.

8. The compound of claim 6 wherein the heavy metal is Ir.

9. The compound of claim 6 wherein the heavy metal is Pt.

10. The compound of claim 1, having the Formula III:

III wherein each $R^{11}$ and $R^{12}$ is independently selected from alkyl, alkenyl, alkynyl, alkylaryl, CN, $CF_3$, $CO_2R$, C(O)R, $NR_2$, $NO_2$, OR, halo, aryl, heteroaryl, substituted aryl, substituted heteroaryl or a heterocyclic group, and additionally, or alternatively, any two adjacent substituted positions together form, independently, a fused 5- to 6-member cyclic group, wherein said cyclic group is cycloalkyl, cycloheteroalkyl, aryl, or heteroaryl, and wherein the fused 5- to 6-member cyclic group cyclic group may be optionally substituted with one or more of alkyl, alkenyl, alkynyl, alkylaryl, CN, $CF_3$, $CO_2R$, C(O)R, $NR_2$, $NO_2$, OR, or halo;

each R is independently alkyl, aryl, or heteroaryl; and subscript a and b are independently selected from 0, 1, 2, and 3.

11. The compound of claim 10, having the formula IV:

IV

12. The compound of claim 1, having the Formula V:

V wherein each $R^{11}$, $R^{12}$, $R^{13}$, and $R^{14}$ is independently selected alkyl, alkenyl, alkynyl, alkylaryl, CN, $CF_3$, $CO_2R$, C(O)R, $NR_2$, $NO_2$, OR, halo, aryl, heteroaryl, substituted aryl, substituted heteroaryl or a heterocyclic group, and additionally, or alternatively, any two adjacent substituted positions together form, independently, a fused 5- to 6-member cyclic group, wherein said cyclic group is cycloalkyl, cycloheteroalkyl, aryl, or heteroaryl, and wherein the fused 5- to 6-member cyclic group cyclic group may be optionally substituted with one or more of alkyl, alkenyl, alkynyl, alkylaryl, CN, $CF_3$, $CO_2R$, $C(O)R$, $NR_2$, $NO_2$, OR, or halo;

each R is independently alkyl, aryl and heteroarl; and subscript a, b, c, and d are independently selected from 0, 1, 2, and 3.

* * * * *